United States Patent
Wang

(10) Patent No.: US 10,272,026 B2
(45) Date of Patent: Apr. 30, 2019

(54) WATER-IN-OIL EMULSION COMPOSITIONS SUITABLE FOR ALTERING THE COLOR OF HAIR

(71) Applicant: L'OREAL, Paris (FR)

(72) Inventor: Jeffrey Wang, Jersey City, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/665,005

(22) Filed: Jul. 31, 2017

(65) Prior Publication Data

US 2019/0029946 A1  Jan. 31, 2019

(51) Int. Cl.
| | | |
|---|---|---|
| A61Q 5/10 | (2006.01) | |
| A61K 8/893 | (2006.01) | |
| A61K 8/41 | (2006.01) | |
| A61K 8/06 | (2006.01) | |
| A61K 8/34 | (2006.01) | |

(52) U.S. Cl.
CPC .............. *A61K 8/893* (2013.01); *A61K 8/064* (2013.01); *A61K 8/342* (2013.01); *A61K 8/415* (2013.01); *A61Q 5/10* (2013.01)

(58) Field of Classification Search
CPC .......... A61Q 5/10; A61K 8/064; A61K 8/342; A61K 8/415
See application file for complete search history.

(56) References Cited

U.S. PATENT DOCUMENTS

| | | |
|---|---|---|
| 5,665,368 A | 9/1997 | Lentini et al. |
| 5,817,155 A | 10/1998 | Yasuda et al. |
| 6,315,989 B1 | 11/2001 | Narasimhan et al. |
| 6,528,045 B1 | 3/2003 | Golinski et al. |
| 6,703,004 B2 | 3/2004 | Narasimhan et al. |
| 6,905,694 B1 | 6/2005 | Modi |
| 6,939,536 B2 | 9/2005 | Chen et al. |
| 6,951,642 B2 | 10/2005 | Scholz et al. |
| 7,030,203 B2 | 4/2006 | Mosbey et al. |
| 7,833,289 B1 | 11/2010 | Johnson et al. |
| 8,029,812 B2 | 10/2011 | Sunkara |
| 2002/0119111 A1 | 8/2002 | Kilgour et al. |
| 2003/0113281 A1 | 6/2003 | Rungta |
| 2004/0151679 A1 | 8/2004 | Mogilevich |
| 2004/0241114 A1 | 12/2004 | Gupta |
| 2005/0039271 A1 | 2/2005 | Schulze zur Wiesche et al. |
| 2005/0125913 A1* | 6/2005 | Narasimhan ......... A61K 8/0295 8/405 |
| 2005/0244353 A1 | 11/2005 | Lendlein et al. |

(Continued)

FOREIGN PATENT DOCUMENTS

| | | |
|---|---|---|
| CH | 445722 A | 10/1967 |
| DE | 10135501 A1 | 1/2003 |

(Continued)

*Primary Examiner* — Eisa B Elhilo

(74) *Attorney, Agent, or Firm* — Polsinelli PC (L'Oreal USA)

(57) ABSTRACT

Provided are water-in-oil emulsion compositions which comprise:
  a. an alkalizing agent;
  b. a dimethicone surfactant;
  c. a fatty alcohol having a C16-36 alkyl group;
  d. an amphoteric surfactant;
  e. a waxy ether or a waxy ester; and
  f. a thickener.
Such compositions may further comprise a hair colorant compound comprising an oxidation dye, and are suitable as a hair color-altering composition. Also provided are kits and methods of using said compositions.

25 Claims, 4 Drawing Sheets

(56) References Cited

U.S. PATENT DOCUMENTS

| | | | |
|---|---|---|---|
| 2006/0078524 A1 | 4/2006 | Midha et al. | |
| 2006/0093571 A1 | 5/2006 | Glinski | |
| 2006/0112503 A1 | 6/2006 | Hatano et al. | |
| 2007/0009465 A1 | 1/2007 | Lendlein et al. | |
| 2007/0220684 A1 | 9/2007 | Narasimhan | |
| 2007/0292460 A1 | 12/2007 | Schiemann et al. | |
| 2007/0297992 A1 | 12/2007 | Schiemann et al. | |
| 2008/0038206 A1 | 2/2008 | Wilfried et al. | |
| 2008/0081024 A1 | 4/2008 | Beasley et al. | |
| 2008/0112897 A1 | 5/2008 | Schiemann et al. | |
| 2008/0112898 A1 | 5/2008 | Schiemann et al. | |
| 2008/0124293 A1 | 5/2008 | Hoffmann et al. | |
| 2008/0317795 A1 | 12/2008 | Traynor et al. | |
| 2009/0098079 A1 | 4/2009 | Schiemann et al. | |
| 2010/0233104 A1 | 9/2010 | Drake et al. | |
| 2013/0171080 A1 | 7/2013 | Sarkar et al. | |
| 2013/0202546 A1* | 8/2013 | Howell | A61K 8/8152 424/70.16 |
| 2015/0283053 A1* | 10/2015 | Odman Schmid | A61K 8/31 8/416 |

FOREIGN PATENT DOCUMENTS

| | | |
|---|---|---|
| EP | 0873108 B1 | 4/1998 |
| EP | 1255827 B8 | 8/2001 |
| EP | 1583512 B3 | 6/2004 |
| EP | 1624851 B1 | 12/2004 |
| EP | 1584323 B1 | 10/2005 |
| EP | 1791516 B2 | 12/2005 |
| KR | 20070053924 A | 5/2007 |
| WO | WO9606878 A1 | 3/1996 |
| WO | WO04108108 A1 | 8/2003 |
| WO | WO07002044 A1 | 12/2006 |
| WO | WO07110415 A2 | 10/2007 |

* cited by examiner

WATER-IN-OIL EMULSION COMPOSITIONS SUITABLE FOR ALTERING THE COLOR OF HAIR

TECHNICAL FIELD

The present disclosure generally relates to compositions for use in coloring the hair, and more particularly to water-in-oil emulsion compositions suitable for such uses.

BACKGROUND

The process of changing the color of hair, can involve depositing an artificial color onto the hair which provides a different shade or color to the hair, and/or lifting the color of the hair, such as lightening the color of dark hair to lighter shades.

Imparting a color change or color effect on hair can be done using permanent, demi-permanent, and semi-permanent or temporary hair coloring products. Conventional permanent hair coloring products are dye compositions comprising oxidation dye precursors, which are also known as primary intermediates or couplers. These oxidation dye precursors are colorless or weakly colored compounds which, when combined with oxidizing products, give rise to colored complexes by a process of oxidative condensation. The oxidizing products (i.e., developers) conventionally use peroxides such as hydrogen peroxide as oxidizing agents. Such permanent hair color products also contain ammonia or other alkalizing agents such as monoethanolamine (MEA) which causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair. Demi-permanent dyeing also utilizes oxidation dye precursors, but are often used with a low volume developer (e.g., 2-3% hydrogen peroxide), as well as MEA. Semi-permanent dyeing uses direct dyes, which are nonionic or ionic dyes and colored compounds capable of producing a more or less pronounced change of the natural color of the hair, resistant to shampoo-washing several times. These dyes may or may not be used in the presence of an oxidizing agent. In contrast with oxidation dye precursors, a direct dye is a relatively voluminous molecule that does not penetrate easily into the core of the fiber.

Permanent hair color has the obvious advantage of the most durable of the hair color treatments described above. However, some of these active ingredients can be harsh and cause adverse reactions in users. Thus, there is a desire to provide hair color compositions which have the added benefits of better conditioning, scalp comfort, and the need for less dyes.

SUMMARY

One aspect of the invention pertains to a hair color-altering composition comprising:
a. an alkalizing agent;
b. a dimethicone surfactant;
c. a fatty alcohol having a $C_{16-36}$ alkyl group;
d. an amphoteric surfactant;
e. a waxy ether or a waxy ester; and
f. a thickener,
wherein the composition is in the form of a water-in-oil emulsion.

In one or more embodiments, the composition further comprises a hair colorant compound comprising an oxidation dye. In some embodiments, the composition has a pH of greater than about 7. In one or more embodiments, the alkalizing agent is selected from the group consisting of $NH_4OH$, monoethanolamine, and combinations thereof. In some embodiments, the composition comprises less than 20% by weight ammonia. In one or more embodiments, the oxidation dye is present in an amount of from about 0.05 to about 4. In some embodiments, the oxidation dye selected from the group consisting of para-phenylenediamines, bis(phenyl)alkylenediamines, para-aminophenols, ortho-aminophenols, heterocyclic bases, the addition salts thereof, and combinations thereof. In one or more embodiments, the dimethicone surfactant comprises an alkoxylated dimethicone. In some embodiments, the dimethicone surfactant comprises an alkoxylated dimethicone having ethoxy and/or propoxy groups. In one or more embodiments, the dimethicone surfactant has about 5-50 moles of ethoxy and/or propoxy groups. In some embodiments, the dimethicone surfactant has about 5-20 moles of ethoxy groups and 5-20 moles propoxy groups. In one or more embodiments, the fatty alcohol has an HLB value of less than 7. In some embodiments, the fatty alcohol has a $C_{18-26}$ alkyl group. In one or more embodiments, the amphoteric surfactant comprises an alkylamido alkylamine. In some embodiments, the alkylamido alkylamine comprises sodium cocoamphoacetate. In one or more embodiments, the waxy ether or waxy ester comprises PEG-30 dipolyhydroxystearate. In some embodiments, the thickener comprises hydrogenated vegetable oil, ozokerite, disteardimonium hectorite or combinations thereof. In one or more embodiments, the composition further comprises an inorganic salt.

In some embodiments, the composition comprises:
a. about 0.01 to 5% by weight of the hair colorant compound comprising an oxidation dye;
b. about 0.01 to 15% by weight of the alkalizing agent;
c. about 0.1 to 10% by weight of the dimethicone surfactant;
d. about 0.1 to 10% by weight of the fatty alcohol having a C16-36 alkyl group;
e. about 0.1 to 10% by weight of the amphoteric surfactant;
f. about 0.1 to 10% by weight of the waxy ether or waxy ester; and
g. about 0.1 to 10% by weight of the thickener.
wherein the composition is a water-in-oil emulsion.

In one or more embodiments, the composition comprises:
a. about 0.05 to 5% by weight of the hair colorant compound comprising an oxidation dye;
b. about 0.01 to 25% by weight of the alkalizing agent;
c. about 1 to 5% by weight of the dimethicone surfactant;
d. about 1 to 5% by weight of behenyl alcohol;
e. about 1 to 5% by weight of sodium cocoamphoacetate;
f. about 1 to 5% by weight of the waxy ether or waxy ester; and
g. about 1 to 5% by weight of the disteardimonium hectorite.
wherein the composition is a water-in-oil emulsion.

Another aspect of the invention pertains to kits comprising the compositions described herein. In one or more embodiment, the kit comprises
a. a first container comprising any of the hair color-altering compositions described herein; and
b. a second container comprising a developer comprising hydrogen peroxide.

Yet another aspect of the invention pertains to methods of altering the color of hair. In some embodiments, the method comprises applying any of the hair color-altering compositions described herein to hair.

Another aspect of the invention pertains to a method of making a water-in-oil emulsion. In one or more embodiments, the method comprises:
  a. preparing an oil phase by combining while heating:
     i. an oil base;
     ii. a dimethicone surfactant;
     iii. a fatty alcohol having a C16-36 alkyl group;
     iv. a waxy ether or a waxy ester; and
     v. a thickener;
  b. preparing a water phase by combining while heating:
     i. water
     ii. an amphoteric surfactant
     iii. optionally, a salt
  c. adding the water phase into the oil phase and mixing the water phase and oil phase;
  d. optionally, adding additional thickener;
  e. adding a hair colorant compound comprising an oxidation dye, wherein the composition is a water-in-oil emulsion. In one or more embodiments, the method further comprises adding a hair colorant compound comprising an oxidation dye after adding the water phase into the oil phase.

DETAILED DESCRIPTION

Figure 1:
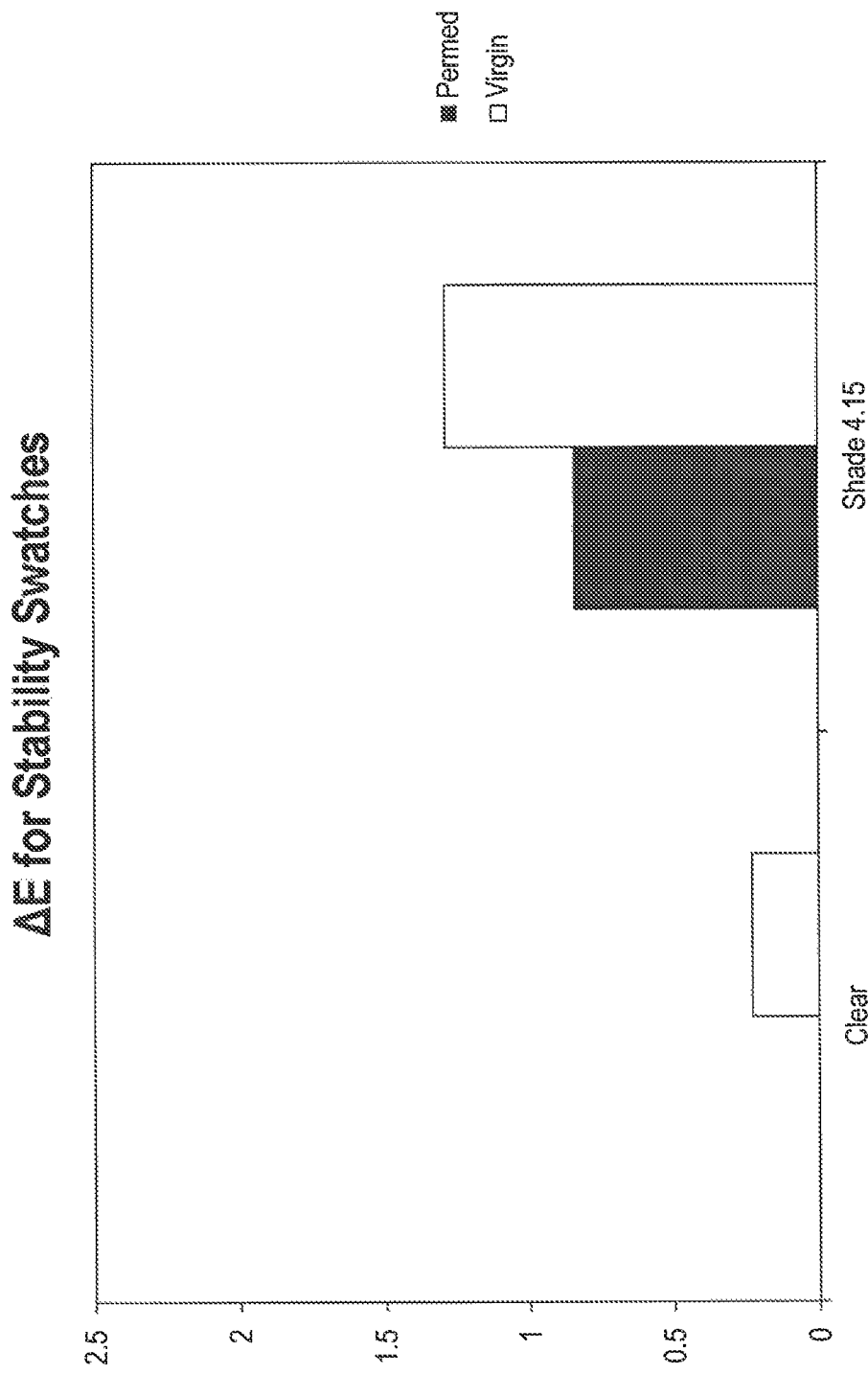
FIG. 1 shows ΔE measurements for a water-in-oil emulsion composition in accordance with one or more embodiments of the invention.

Other than in the operating examples, or where otherwise indicated, all numbers expressing quantities of ingredients and/or reaction conditions are to be understood as being modified in all instances by the term "about" which can encompass ±10%, ±8%, ±6%, ±5%, ±4%, ±3%, ±2%, ±1%, or ±0.5%.

All numbers expressing pH values are to be understood as being modified in all instances by the term "about" which encompasses up to ±3%.

"At least one" as used herein means one or more and thus includes individual components as well as mixtures/combinations.

The term "altering the color" or "color-altering" as used herein may refer to lifting or lightening the color of hair. It can also refer to dyeing or coloring hair or depositing color onto the hair. In certain instances, it refers to lifting or lightening the color of hair and depositing color onto the hair in one treatment.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

The term "neutralized" as used herein is intended to mean that the 3-butoxypropylamine is protonated with a $H^+$ (proton) coming from the diacid(s).

The term "substantially free of (a component)" as defined herein means that the system or composition contains no appreciable amount of the component, for example, no more than about 1% by weight, no more than about 0.5% by weight, or no more than about 0.3% by weight, such as no more than about 0.1% by weight, based on the weight of the composition.

The term "free" or "completely free of (a component)" as defined herein means that the composition does not contain the component in any measurable degree by standard means.

Color-Altering Compositions

As described herein, the disclosure relates to hair color-altering compositions comprising an alkalizing agent, a dimethicone surfactant, a fatty alcohol having a $C_{16-36}$ alkyl group, an amphoteric surfactant, a waxy ether or a waxy ester, and a thickener. It has been surprisingly discovered that such compositions can be prepared in the form of a water-in-oil emulsion.

Such water-in-oil emulsion compositions are suitable for use in the hair color art. Thus, in some embodiments, the composition comprises a hair colorant compound comprising an oxidation dye. Water-in-oil emulsion compositions, sometimes used in skin care and makeup applications, are not generally known in the hair color art. These compositions have the benefits of better conditioning, scalp comfort, and the need for less dyes compared to conventional hair color compositions. While not wishing to be bound to any particular theory, it is thought that such benefits derive from higher effective concentration and/or protection from oxidizers in the atmosphere as a result of the water-in-oil system. It is also thought that these compositions have the benefits of being soothing to the skin as well as being emollients, which could provide better scalp comfort in a hair color product. These compositions may also form oily films on the skin, which could provide a conditioning layer to the hair.

As used herein, "emulsion" refers to a system in which one liquid is dispersed in an otherwise immiscible liquid medium. Stable emulsions involve the use of surfactants, which act as the interfacial boundaries between emulsified droplet and continuous phase. As used herein, the term "water-in-oil emulsion" (W/O emulsions) refers to an emulsion composition in which the emulsified phase is aqueous and continuous phase is oil-based. Such emulsions are distinguished from "oil-in-water emulsion" (O/W emulsions) which refers to emulsions in which the oil is the emulsified phase and the continuous phase is aqueous. The water-in-oil emulsions may have droplets in the micrometer range (e.g., 10-50 micrometer). The base oil in the water-in-oil comprises at least one oil. The oil can comprise one or more hydrocarbon oil(s) in a proportion of between 0.1 and 40, 45, 50, 55, 60, 65, 70, 75, 80, 85 or 90% by weight with respect to the total weight of the composition. Mention will be made, as hydrocarbon oil, of: any fluid oil (or mixture of oils) which is stable at the usual temperature of use of cosmetic products and which is pharmaceutically or cosmetically acceptable, such as vegetable or animal oils, mineral or synthetic oils, fluorinated oils and triglycerides of C12-C18 fatty acids.

Mention may be made, among modified or unmodified vegetable or animal oils, of, for example, sweet almond oil, avocado oil, castor oil, olive oil, jojoba oil, sunflower oil, wheat germ oil, sesame oil, groundnut oil, grape seed oil, soya oil, rapeseed oil, safflower oil, coconut oil, maize oil, hazelnut oil, karite butter, palm oil, apricot kernel oil, or calophyllum oil. Mention may be made, among mineral oils, of, for example, liquid paraffin. Mention may be made, among synthetic oils, of especially isoparaffins and polyisobutenes.

Because the phases are reversed in the two types of emulsions, water-in-oil emulsions behave quite differently from oil-in-water emulsions. For example, with the water-in-oil emulsions described herein, a unique cream texture is provided, with the dye aromatic molecules contained in the water droplet phase, not the continuous phase. The dyes are thus more concentrated in the water emulsified phase, allowing the dye load to be decreased from traditional dispersion creams or oil-in-water creams but still produce similar shades.

As such, in one or more embodiments, the compositions described herein contain less than 1, 0.5, 0.1, 0.05 or 0.01% by weight of the composition of surfactants known to produce oil-in-water emulsions. In further embodiments, the composition does not comprise any surfactants known to produce oil-in-water emulsions. In one or more embodiments, such surfactants which are known to produce oil-in-water emulsions are those which have relatively high hydrophile-lipophile balance (HLB) values (e.g., above 8, 10, 15 or 20). Some examples of surfactants known to produce oil-in-water emulsions include sodium lauryl sulfate (HLB of about 40) and potassium oleate (HLB of about 20).

Colorant Compounds

As described herein, in various exemplary and non-limiting embodiments, color-altering compositions may optionally comprise at least one colorant compound chosen from one or more oxidation dyes. The oxidation dyes are generally chosen from one or more oxidation bases optionally combined with one or more couplers.

By way of example, the oxidation bases may be chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-methoxymethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethyl amino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases can include the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol; 2-(4-dimethylpyperazinium-1-yl)-3-amino-pyrazolo[1,5-a]pyridine; and the addition salts thereof.

More particularly, oxidation bases can be selected from 3-aminopyrazolo-[1,5-a]-pyridines and preferably substituted on carbon atom 2 by:

one (di)(C1-C6)(alkyl)amino group wherein said alkyl group can be substituted by at least one hydroxy, amino, imidazolium group;

one heterocycloalkyl group containing from 5 to 7 members chain, and from 1 to 3 heteroatoms, potentially cationic, potentially substituted by one or more (C1-C6)alkyl, such as di(C1-C4)alkylpiperazinium; or one (C1-C6)alkoxy potentially substituted by one or more hydroxy groups such as α-hydroxyalkoxy, and the addition salts thereof.

Among the pyrimidine derivatives that may be mentioned are the compounds described, for example, in the patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole, and the addition salts thereof 4,5-Diamino-1-(β-methoxyethyl)pyrazole may also be used.

A 4,5-diaminopyrazole will preferably be used, and even more preferentially 4,5-diamino-1-(β-hydroxyethyl)pyrazole and/or a salt thereof.

Pyrazole derivatives that may also be mentioned include diamino-N,N-dihydro-pyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a] pyrazol-1-one, 2-amino-3-dimethylamino-6,7-dihydro-1H, 5H-pyrazolo[1,2-a]pyrazol-1-one, 2,3-diamino-5,6,7,8-tetrahydro-1H, 6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

2,3-Diamino-6,7-dihydro-1H,5H-pyrazolo[1,2-a]pyrazol-1-one and/or a salt thereof will preferably be used.

4,5-Diamino-1-(β-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Compositions may optionally further comprise one or more couplers advantageously chosen from those conventionally used in the dyeing or coloring of keratinous substrates.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N-(β-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxy-ethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzo-morpholine, 3,5-diamino-2,6-dimethoxypyridine, 1-N-(β-hydroxyethyl)amino-3,4-methylenedioxybenzene, 2,6-bis(β-hydroxyethylamino) toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used are chosen from the addition salts with an acid such as the hydrochlorides, hydrobromides, sulfates, citrates, succinates, tartrates, lactates, tosylates, benzenesulfonates, phosphates and acetates.

The oxidation base(s) may be present in an amount ranging from about 0.001% to 10% by weight, such as from about 0.005% to 5% by weight, relative to the total weight of the composition comprising the system in which it is present.

The coupler(s), if they are present, may be present in an amount ranging from about 0.001% to 10% by weight, such as from about 0.005% to 5% by weight, relative to the total weight of the system or composition comprising the system in which it is present.

Compositions according to embodiments of the disclosure may optionally comprise one or more synthetic or natural direct dyes, for example chosen from anionic and nonionic species, preferably cationic or nonionic species, either as sole dyes or in addition to the oxidation dye(s).

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

Preferably direct dyes are cationic direct dyes. Mention may be made of the hydrazono cationic dyes of formulas (Va) and (V'a), the azo cationic dyes (VIa) and (VI'a) and the diazo cationic dyes (VIIa) below:

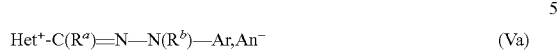  (Va)

  (V'a)

  (VIa)

  (VI'a) and

  (VIIa)

in which formulas (Va), (V'a), (VIa), (VI'a) and (VIIa):

Het$^+$ represents a cationic heteroaryl moiety, preferably bearing an endocyclic cationic charge, such as imidazolium, indolium or pyridinium, optionally substituted preferentially with one or more $(C_1-C_8)$ alkyl groups such as methyl;

Ar$^+$ representing an aryl moiety, such as phenyl or naphthyl, bearing an exocyclic cationic charge, preferentially ammonium, particularly tri$(C_1-C_8)$alkylammonium such as trimethylammonium;

Ar represents an aryl group, especially phenyl, which is optionally substituted, preferentially with one or more electron-donating groups such as i) optionally substituted $(C_1-C_8)$alkyl, ii) optionally substituted $(C_1-C_8)$alkoxy, iii) (di)$(C_1-C_8)$(alkyl)amino optionally substituted on the alkyl group(s) with a hydroxyl group, iv) aryl$(C_1-C_8)$alkylamino, v) optionally substituted N—$(C_1-C_8)$alkyl-N-aryl$(C_1-C_8)$alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups $(C_1-C_8)$alkyl, hydroxyl or $(C_1-C_8)$alkoxy;

Ar" is an optionally substituted (hetero)aryl group such as phenyl or pyrazolyl, which are optionally substituted, preferentially with one or more groups $(C_1-C_8)$alkyl, hydroxyl, (di)$(C_1-C_8)$(alkyl)amino, $(C_1-C_8)$alkoxy or phenyl;

R$^a$ and R$^b$, which may be identical or different, represent a hydrogen atom or a group $(C_1-C_8)$alkyl, which is optionally substituted, preferentially with a hydroxyl group; or alternatively the substituent R$^a$ with a substituent of Het$^+$ and/or R$^b$ with a substituent of Ar and/or R$^a$ with R$^b$ form, together with the atoms that bear them, a (hetero)cycloalkyl; particularly, R$^a$ and R$^b$ represent a hydrogen atom or a group $(C_1-C_4)$alkyl, which is optionally substituted with a hydroxyl group;

An$^-$ represents an anionic counter-ion such as mesylate or halide.

In particular, mention may be made of the azo and hydrazono cationic dyes bearing an endocyclic cationic charge of formulae (Va), (V'a) and (VIa) as defined previously. More particularly mention may be made of those of formulae (Va), (V'a) and (VIa) derived from the dyes described in patent applications WO 95/15144, WO 95/01772 and EP-714954.

In various embodiments, the cationic part is derived from the following derivatives:

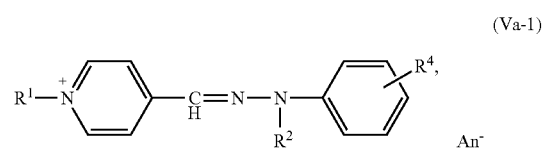  (Va-1)

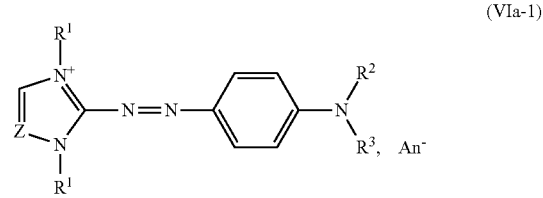  (VIa-1)

wherein in formulae (Va-1) and (VIa-1):

R$^1$ representing a $(C_1-C_4)$ alkyl group such as methyl;

R$^2$ and R$^3$, which are identical or different, represent a hydrogen atom or a $(C_1-C_4)$alkyl group, such as methyl; and R$^4$ represents a hydrogen atom or an electron-donating group such as optionally substituted $(C_1-C_8)$alkyl, optionally substituted $(C_1-C_8)$alkoxy, or (di)$(C_1-C_8)$(alkyl)amino optionally substituted on the alkyl group(s) with a hydroxyl group; particularly, R$^4$ is a hydrogen atom, Z represents a CH group or a nitrogen atom, preferentially CH;

An$^-$ represents an anionic counter-ion such as mesylate or halide.

The dye of formulae (Va-1) and (VIa-1) can be chosen from Basic Red 51, Basic Yellow 87 and Basic Orange 31 or derivatives thereof:

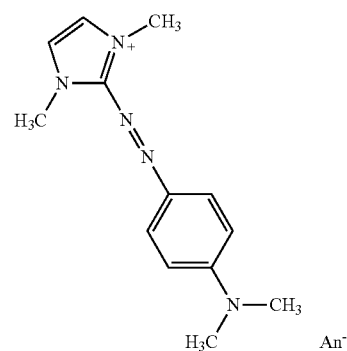

Basic Red 51

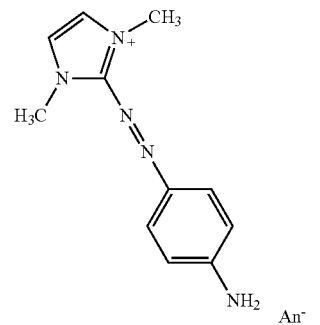

Basic Orange 31

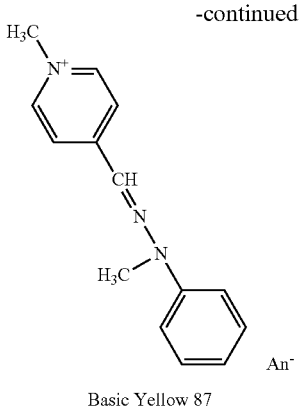

Basic Yellow 87

Among the natural direct dyes, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used. When they are present, the one or more direct dyes more particularly represent from about 0.001% to 10% by weight, such as from about 0.005% to 5% by weight, of the total weight of the system or composition comprising the system in which it is present.

The color-altering composition may also comprise a cosmetically acceptable carrier. The cosmetically acceptable carrier may, for example, be present in the color-altering composition in an amount ranging from about 1% to about 40% by weight, such as from about 5% to about 35% by weight, or about 10% to about 30% by weight of the color-altering composition.

Alkalizing Agents

The compositions described herein comprise one or more alkalizing agents. The alkalizing agents are generally present in the water phase of the resulting emulsion.

The alkalinity of the hair color-altering composition may be derived from one or more alkalizing agents. In some embodiments, the alkalizing agent may ammonia or an ammonia gas-generating compound and/or an amine or ammonium-based compound in amounts sufficient to make such compositions alkaline. In further embodiments, the alkalizing agent may be selected from alkanolamines, such as monoethanolamine (MEA) and isopropanolamine. Alkalinity may be derived from ammonium compounds as well (e.g., $NH_4OH$).

The one or more alkalizing agents may be present in amounts ranging from greater than about 0, or from 1, 2, 3, 4, 5, 10 to about 5, 10, 13, 15, 18, 20, 25 or 30% by weight of the total composition.

The hair color-altering composition may have a pH that is alkaline. Exemplary pH's include 7, 8, 9, 10, 11, 12, 13 or 14. In some embodiments, the pH of the hair color-altering composition may range from about 7, 8, or 9 to about 9, 10, 11 or 12.

Dimethicone Surfactant

The compositions described herein comprise one or more dimethicone surfactants. As used herein, the term "dimethicone surfactant" means a compound which contains dimethicone or dimethicone monomers and is suitable as a surfactant.

The dimethicone surfactants may act as the primary surfactant in the compositions, meaning these surfactants are the surfactants responsible for the biggest decrease in surface tension. The dimethicone surfactants may be added to the oil phase during preparation of the compositions described herein, but may exist on the border of the water and oil phases in the emulsion due to their surfactant nature.

Such dimethicone surfactants may also comprise additional monomer functionality. For example, in some embodiments, the dimethicone surfactant comprises alkoxylation (e.g., ethoxylation, propoxylation, and combinations thereof). Non-limiting examples of suitable dimethicone surfactants, include, but are not limited to: bis-PEG/PPG-14/14 dimethicone and dimethicone/PEG-10/15 cross polymer. These surfactants are available in dimethicone blends from Evonik Goldschmidt under tradename ABIL EM 97S and from Shin Etsu under tradename KSG-210, respectively.

In one or more embodiments, the dimethicone surfactant is present at an amount of from about 0.1, 0.5, 1, 2, 3 to about 4, 5, 6, 7, 8, 9 or 10% by weight of the total composition.

Fatty Alcohol

The compositions described herein also comprise one or more fatty alcohol having a $C_{16-36}$ alkyl group. It is thought that the fatty alcohol aids in stability of the water-in-oil emulsion. Together with the dimethicone surfactant, it is also thought that these ingredients are soothing the scalp, which may be irritated by the presence of ammonia in hair color compositions. The fatty alcohols will generally be located in the oil phase of the water-in-oil emulsions. In some embodiments, the fatty alcohol has a hydrophile-lipophile balance (HLB) value of less than about 7, 6, 5, 4 or 3, or from about 1, 2, 3, 4 or 5 to about 4, 5, 6 or 7.

In one or more embodiments, the fatty alcohol is selected from stearyl alcohol, myristyl alcohol, arachidyl alcohol, cetyl alcohol, behenyl alcohol, cetearyl alcohol (a blend of cetyl and stearyl alcohols), and combinations thereof. In further embodiments, the fatty alcohol is selected from stearyl alcohol, behenyl alcohol, cetearyl alcohol, and combinations thereof.

In one or more embodiments, the fatty alcohol is present at an amount of from about 0.1, 0.5, 1, 2, 3 to about 4, 5, 6, 7, 8, 9 or 10% by weight of the total composition.

Amphoteric Surfactant

The compositions described herein also comprise one or more amphoteric surfactants. These amphoteric surfactants are thought to act as secondary surfactants, which aid the primary surfactant in decreasing surface tension. The amphoteric surfactants may be added to the aqueous phase during preparation of the compositions described herein, but may exist on the border of the water and oil phases in the emulsion due to their surfactant nature.

In one or more embodiments, the amphoteric surfactant is selected from alkylamido alkylamines and alkylated amino acids. In some embodiments, the amphoteric surfactant may comprise betaines, sultaines, hydroxysultaines, alkyl amphodiacetates, alkyl amphodipropionates, and imidazolines, or salts thereof. In one or more embodiments, the amphoteric surfactant is selected from sodium cocoamphoacetate.

In one or more embodiments, the amphoteric surfactant is present at an amount of from about 0.1, 0.5, 1, 2, 3 to about 1, 1.5, 2, 2.5, 3, 3.5, 4, 4.5 or 5% by weight of the total composition.

Waxy Ether/Ester

The compositions described herein also comprise one or more waxy ethers or waxy esters. These waxy ethers/esters are located in the oil phase of the water-in-oil emulsion.

In some embodiments, the waxy ester comprises the ester of a fatty acid and a fatty alcohol. Such esters generally have the structure RCOOR', wherein the R groups may range from C12 to C34, or more specifically C20 to C34.

In some embodiments, the waxy ether comprises an alkoxylated fatty alcohol. The fatty alcohol may contain more than 12, 16 or 20 carbons up to 34 or 40 carbon atoms. In further embodiments, the alkoxylation means the presence of PPG and/or PEG groups. In some embodiments, on average, the number of PPG and/or PEG units may range from 2 to 40, or 2 to 30.

In one or more embodiments, the waxy ether/ester comprises cetyl palmitate, sorbitan stearate, glyceryl oleate, glyceryl oleate, sorbitan oleate, sorbitan sesquioleate, PEG-8 beeswax, polyclyeryl-3 diisostearate, steareth-10, steareth-2, glyceryl lauryl ether, glyceryl monostearate, sorbitan stearate, PEG-30 dipolyhydroxystearate, and combinations thereof.

In one or more embodiments, the waxy ether/ester is present at an amount of from about 0.1, 0.5, 1, 2, 3 to about 4, 5, 6, 7, 8, 9 or 10% by weight of the total composition.

Thickener

The compositions described herein also comprise one or more thickeners. In some embodiments, the thickeners have a high melting point (i.e., 70° C. or above). These thickeners are thought to help with droplet stability in the emulsion by thickening the continuous oil phase so that emulsified droplets cannot undergo coalescence. In one or more embodiments, the thickener is a non-polar thickener. In some embodiments, the thickener is chosen from hydrogenated oils, waxes ozokerits and/or hectorites. Thus, in further embodiments, the thickener is chosen from hydrogenated vegetable oil, ozokerite, disteardimonium hectorite, and/or beeswax.

In one or more embodiments, the thickener is present at an amount of from about 0.1, 0.5, 1, 2, 3 to about 4, 5, 6, 7, 8, 9 or 10% by weight of the total composition.

Salts

In one or more embodiments, an ionic salt may be added to provide ionic charge repulsion of the water droplets with dyes. In some embodiments, the ionic salt may be a water-soluble metal salt. In one or more embodiments, the salts are selected from the group consisting of zinc chloride, magnesium chloride, ferrous chloride, manganese chloride, cupric chloride, calcium chloride, cobalt dichloride, zinc sulfate, magnesium sulfate, ferrous sulfate, manganese sulfate, copper sulfate, cobalt sulfate, zinc acetate, magnesium acetate, ferrous acetate, manganese acetate, cupric acetate, calcium acetate, cobalt acetate, magnesium citrate, ferrous citrate, manganese citrate, calcium chloride, calcium citrate and mixtures thereof.

Developer Composition

When the color-altering composition comprises a separate developer composition, the developer composition may comprise hydrogen peroxide. The developer composition may also optionally comprise a cosmetically acceptable carrier.

In various exemplary embodiments, hydrogen peroxide is present in an amount of at least about 1% by weight, based on the total weight of the developer composition. In further embodiments, hydrogen peroxide is present in an amount ranging from about 0.1% to about 80% by weight, such as from about 1.0% to about 75% by weight, or from about 2% to about 10% by weight, based on the total weight of the developer composition. In further exemplary embodiments, the hydrogen peroxide may be present in the developer composition in an amount ranging from about 2% to about 25%, such as about 4% to about 20%, about 6% to about 15%, or about 7% to about 10%.

The cosmetically acceptable carrier of the developer composition may, for example, be present in an amount ranging from about 0.5% to about 99% by weight, such as from about 5% to about 95% by weight, relative to the total weight of the developer composition.

The pH of the developer composition can range from about 1 to about 5, such as from about 2 to about 4, and it may be adjusted to the desired value using pH adjusters that are well known in the art in the cosmetic treatment of keratin fibers, including, for example, those described herein.

The developer composition may be in the form of a powder, gel, liquid, foam, lotion, cream, mousse, and emulsion.

According to various exemplary embodiments, the developer composition may be anhydrous. Optionally, water may be added as an activator, by mixing it with the developer composition.

The developer composition may, in various embodiments, comprise additional components such as, for example, at least one auxiliary ingredient chosen from rheology-modifying agents, chelants, fatty substances, ceramides, alkoxyaminosilicones, and silanes, and any other component known in the art to be useful in a developer composition.

In at least one exemplary embodiment, the color-altering composition may be mixed with the developer composition to form the color-altering composition right before (e.g. within a few minutes before) applying the color-altering composition onto the hair.

In one exemplary embodiment, the color-altering composition and developer composition may be combined to form the lightening composition in a ratio of color-altering composition composition to developer composition ranging from about 1:1 to about 1:5, such as from about 1:1 to about 1:2, or about 1:2 to about 1:4.

Auxiliary Agents

Auxiliary ingredients may be added to the color-altering composition. Exemplary auxiliary ingredients useful in the color-altering composition according to various embodiments of the disclosure include, but are not limited to, rheology-modifying agents, bleach activators and co-bleach activators, direct dyes, chelants (e.g., EDTA), antioxidants (e.g., erythorbic acid, sodium metabisulfite) fatty substances, ceramides, alkoxyaminosilicones, silanes, and lift-enhancing agents, such as nitrogen-containing compounds and metal catalyst compounds.

The color-altering composition may also contain acid and alkali pH adjusters, which are well known in the art in the cosmetic treatment of keratin fibers, such as hair. Such pH adjusters include, but are not limited to, sodium metasilicate, silicate compounds, citric acid, ascorbic acid, and carbonate compounds.

Methods of Preparing Color-Altering Compositions

Another aspect of the invention pertains to methods of preparing the water-in-oil emulsions described herein. One advantage of these water-in-oil emulsions is that they may be prepared by chemical means, rather than the very energy-intense physical ones. In one or more embodiments, the method comprises a. preparing an oil phase by combining while heating:
　i. an oil base;
　ii. a dimethicone surfactant;
　iii. a fatty alcohol having a C16-36 alkyl group;
　iv. a waxy ether or a waxy ester; and
　v. a thickener;
b. preparing a water phase by combining while heating:

i. water
ii. an amphoteric surfactant
iii. optionally, a salt
c. adding the water phase into the oil phase and mixing the water phase and oil phase;
d. optionally, adding additional thickener;
e. adding a hair colorant compound comprising an oxidation dye, wherein the composition is a water-in-oil emulsion.

In some embodiments, the method further comprises adding a hair colorant compound comprising an oxidation dye after adding the water phase into the oil phase.

Any of the above composition embodiments may be prepared using the above method. Auxiliary agents, such as chelants, other dyes, and antioxidants can be added after the oil and aqueous phases have been combined.

Kits and Methods of Use

Another aspect of the invention pertains to kits comprising the color-altering compositions described herein. For example, developer may be present in a separate container from the color-altering composition which comprises the fruit enzyme, oxidizing agent, hair colorant and/or oxidizing agent. In such embodiments, the developer and hair color-altering composition are combined just prior to use. The color-altering composition may, in some embodiments, be in a ready-to-use form.

Another aspect of the invention pertains to methods of using the color-altering compositions. The methods comprise applying the compositions described herein to human hair. The color-altering composition may be left on the hair for a period of time sufficient to achieve the desired alteration in hair tone. For example, the color-altering composition may be left on the hair for up to one hour, such as from about 3 minutes to about 45 minutes, from about 5 minutes to about 30 minutes, or from about 10 minutes to about 20 minutes. In further embodiments, the color-altering composition may be left on the hair for a period up to about 30 minutes, such as, for example, from about 1 to about 30 minutes, about 1 to about 10 minutes, or about 1 to about 5 minutes. One skilled in the art will, by considering various factors such as the starting and desired tones of the hair, be able to determine an appropriate amount of time to leave the color-altering composition on the hair in order to achieve the desired alternation in hair tone.

In some embodiments, the color-altering composition may, optionally, be shampooed and/or rinsed off the hair.

EXAMPLES

The ingredient amounts in the composition/formulations described below are expressed in % by weight, based on the total weight of the composition, unless otherwise indicated.

Example 1—Preparation of W/O Emulsion Composition

Water-in-oil emulsion cream compositions having the compositions shown in Tables 1-3 below.

TABLE 1

Inventive Formula 1 (Clear)

| INCI Name | Concentration | |
|---|---|---|
| Magnesium Sulfate | 0.75 | Salt |
| Ammonium Hydroxide | 2.0575 | Active |
| Ethanolamine | 4.7 | Active |
| BIS-PEG/PPG-14/14 Dimethicone | 3.4 | Dimethicone surfactant |
| Glycerin | 5 | Humectant/solvent |
| EDTA | 0.2 | Chelant |
| Dimethicone | 0.6 | Dimethicone |
| Behenyl Alcohol | 4 | Fatty alcohol having a $C_{16-36}$ alkyl group |
| Sodium Cocoamphoacetate | 0.96 | Amphoteric Surfactant |
| PEG-30 Dipolyhydroxystearate | 4 | Waxy ether/ester |
| Sodium Chloride | 0.228 | Salt |
| Water | 30.3045 | Solvent |
| Mineral Oil | 40 | Oil Base |
| Antioxidant | 0.8 | Antioxidant |
| Disteardimonium Hectorite | 3 | Thickener |
| Total | 100 | |

TABLE 2

Inventive Formula 2 (Shade 4.15)

| INCI Name | Concentration | |
|---|---|---|
| Fragrance | 0.8 | Fragrance |
| Magnesium Sulfate | 0.75 | Salt |
| Oxidation Dyes | 1.89608 | Colorant |
| Ammonium Hydroxide | 2.0575 | Active |
| Ethanolamine | 4.603 | Active |
| BIS-PEG/PPG-14/14 Dimethicone | 3.4 | Dimethicone surfactant |
| Dimethicone | 0.6 | Dimethicone |
| Glycerin | 5 | Humectant/solvent |
| EDTA | 0.2 | Chelant |
| Behenyl Alcohol | 4 | Fatty alcohol having a $C_{16-36}$ alkyl group |
| Sodium Cocoamphoacetate | 0.96 | Amphoteric Surfactant |
| PEG-30 Dipolyhydroxystearate | 4 | Waxy ether/ester |
| Sodium Chloride | 0.228 | Salt |
| Antioxidant | 0.80192 | Antioxidant |
| Water | 27.7035 | Solvent |
| Mineral Oil | 40 | Oil Base |
| Disteardimonium Hectorite | 3 | Thickener |
| Total | 100 | |

TABLE 3

Inventive Formula 3 (Shade 6.6)

| INCI US Name | Concentration | |
|---|---|---|
| Fragrance | 0.8 | Fragrance |
| Magnesium Sulfate | 0.75 | Salt |
| Oxidation Dyes | 1.89658 | Colorant |
| Ammonium Hydroxide | 2.0575 | Active |
| Ethanolamine | 4.599 | Active |
| BIS-PEG/PPG-14/14 Dimethicone | 3.4 | Dimethicone surfactant |
| Dimethicone | 0.6 | Dimethicone |
| Glycerin | 5 | Humectant/solvent |
| EDTA | 0.2 | Chelant |
| Behenyl Alcohol | 4 | Fatty alcohol having a $C_{16-36}$ alkyl group |
| Sodium Cocoamphoacetate | 0.96 | Amphoteric Surfactant |
| PEG-30 Dipolyhydroxystearate | 4 | Waxy ether/ester |
| Sodium Chloride | 0.228 | Salt |
| Sodium Metabisulfite | 0.50342 | Antioxidant |
| Water | 27.7055 | Solvent |
| Mineral Oil | 40 | Oil base |
| Erythorbic Acid | 0.3 | Antioxidant |

TABLE 3-continued

Inventive Formula 3 (Shade 6.6)

| INCI US Name | Concentration | |
|---|---|---|
| Disteardimonium Hectorite | 3 | Thickener |
| Total: | 100 | |

The above formulae were created according to the below method:

Oil Phase Preparation: Mineral oil, bis-PEG/PPG-14/14 dimethicone and dimethicone, behenyl alcohol, PEG-30 dipolyhydroxystearate, and disteardimonium hectorite (~25% total mass) were combined in a 1 L beaker. The beaker was placed onto a hot plate with water bath and heated 75-80° C. The Oil Phase was then placed under a Rayneri mixer at 200 RPM w/homgenizer blade (standard 6 cm diameter size). Further disteardimonium hectorite was added (~50% total mass).

Aqueous Phase Preparation: Water (~85-90° C.) was added to a separate 600 mL beaker. Add sodium cocoamphoacetate and magnesium sulfate were added into the water and stirred until dissolved.

Emulsion Preparation: The aqueous phase was slowly poured into the hot oil phase (~80° C.), and the mixer speed was increased up to 400-500 RPM. The mixture became an off-white cream. After all of the water had been added, the remainder of the disteardimonium hectorite was added, and the emulsion mixture mixed for 5 minutes with side sweeping. The hot plate was then removed from the beaker and homogenizer, and water basin emptied. The emulsion mixture was then mixed for 20-30 minutes as the temperature cooled. Once the emulsion mixture reached about 50° C., ethanol amine and glycerin were added, followed by antioxidant/dyes/chelants if present. The water basin was then filled with water at 25° C. The emulsion mixture was then mixed until any dyes were dissolved, and cooled to about 30° C. The mixer speed was increased to ~800-900 rpm. Fragrance (if present) was added at ~25-30° C. QS water. Ammonium hydroxide was added at ~25-30° C., and mixed until incorporated. Once completed, the samples were tubed immediately.

Presence of water-in-oil emulsion was verified by adding Red 40 (water-soluble only) and examining under a microscope. Upon observation, only the water droplets were stained red, with no staining of the continuous oil phase.

Example 2—Stability Testing

The above formulations were tested for stability viscosity, with results shown below in Table 4. Initial viscosity measurements were taken 24 hours after production and either alone ("colorant") or mixed with developer ("mixed with developer") using an RM180 Rheomat. In order to measure stability, viscosities were also taken at 1 month after sitting in both a 25° C. and 45° C. oven, again either alone ("colorant") or mixed with developer ("mixed with developer"). Placing samples in stability chambers at 45 C simulate the aging process of the product on the shelf. Colorant viscosities were measured using the M4 spindle and mix viscosities with the M3 spindle, all at an interval of 30 seconds. Generally, a viscosity of 25-65 is considered to be acceptable for use as hair colorant. As can be seen, the viscosities for the various formulae remained within or very close to the acceptable range. Formula 1 was also visually assessed at 25° C. after two months, and a matte, white cream with no separation observed.

TABLE 4

Stability viscosity measurements for Inventive Formulae 1-2

| | Viscosity Type | Formula 1 (Clear) (dU) | Formula 2 (Shade 4.15) (dU) |
|---|---|---|---|
| Initial | Colorant | 36.7 | 16.6 |
| | Mixed with Developer | 47.5 | 47.7 |
| 1 Month 25° C. | Colorant | 60.0 | 33.5 |
| | Mixed with Developer | 66.9 | 66.0 |
| 1 Month 45° C. | Colorant | 42.7 | 24.4 |
| | Mixed with Developer | 59.7 | 42 |

Formulae 1 and 2 were mixed with developer (20 Vol.) applied to permed and virgin hair swatches and processed for 30 minutes. L*a*b values were then taken for the samples, and ΔE values calculated comparing Formulae 1 and 2 at one month at 25° C. to the same formula at one month at 45° C. The results are shown in FIG. 1. ΔE values less than 2.5 are generally considered to be too small to be visually detected by the unaided eye. Significant color shift indicates instability in the product and makes it unmarketable. These results show that there is no significant color shift in the product of both the Clear and Shade 4.15 W/O Inventive from 25° C. to 45° C. at this simulated portion of its shelf life, indicating stability.

Figure 2:
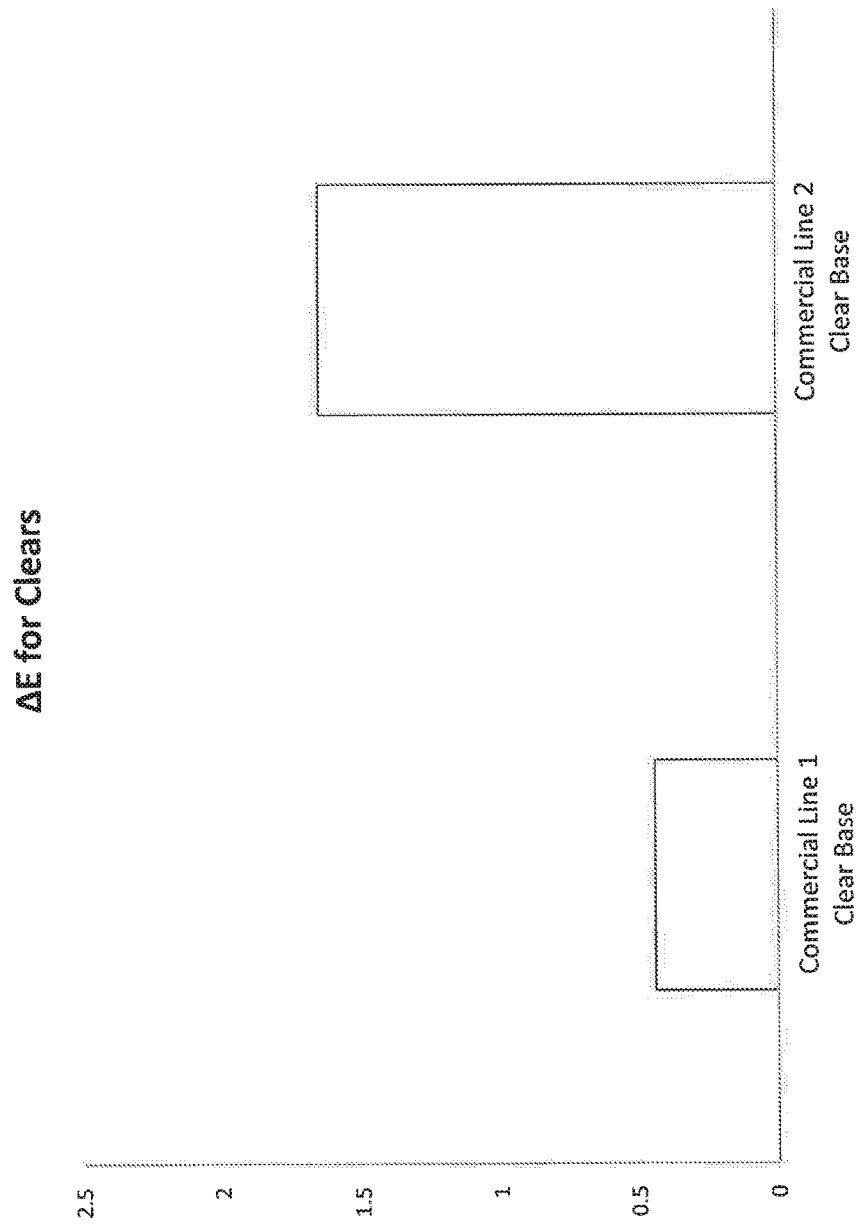
FIG. 2 shows ΔE measurements for two clear commercial base compositions.

For comparison, clear base formulations from two commercially available hair color lines were swatched in the same manner for virgin swatches. The first commercial line (Commercial Line 1) uses a traditional base, (i.e., a dispersion of oils). The traditional base is not considered a true emulsion but more of a dispersion and has a traditional ammonia alkaline system. The second commercial line (Commercial Line 2) uses an Oil Delivery System (ODS). The ODS has a high concentration of oil that is emulsified into an oil in water emulsion that has monoethanolamine as the alkaline agent instead of ammonia. The higher oil percentage allows the monoethanolamine to be concentrated into a smaller reservoir of water and increases its potency and lift without the harsh smell of ammonia. The results of ΔE measurements with respect to the original swatches are shown in FIG. 2.

Example 3—Swatch Testing with Color Base

Four shades (5, 5G, 6R and 6A) were selected from Commercial Line 1. The dye amounts/combinations were taken from the commercial line and incorporated into the inventive water-in-oil emulsion base.

Similarly, four shades (5, 6.33, 6.6, and 6.11) were selected from Commercial Line 2. The dye amounts/combinations were taken from the commercial line and incorporated into the inventive water-in-oil emulsion base.

Figure 3:
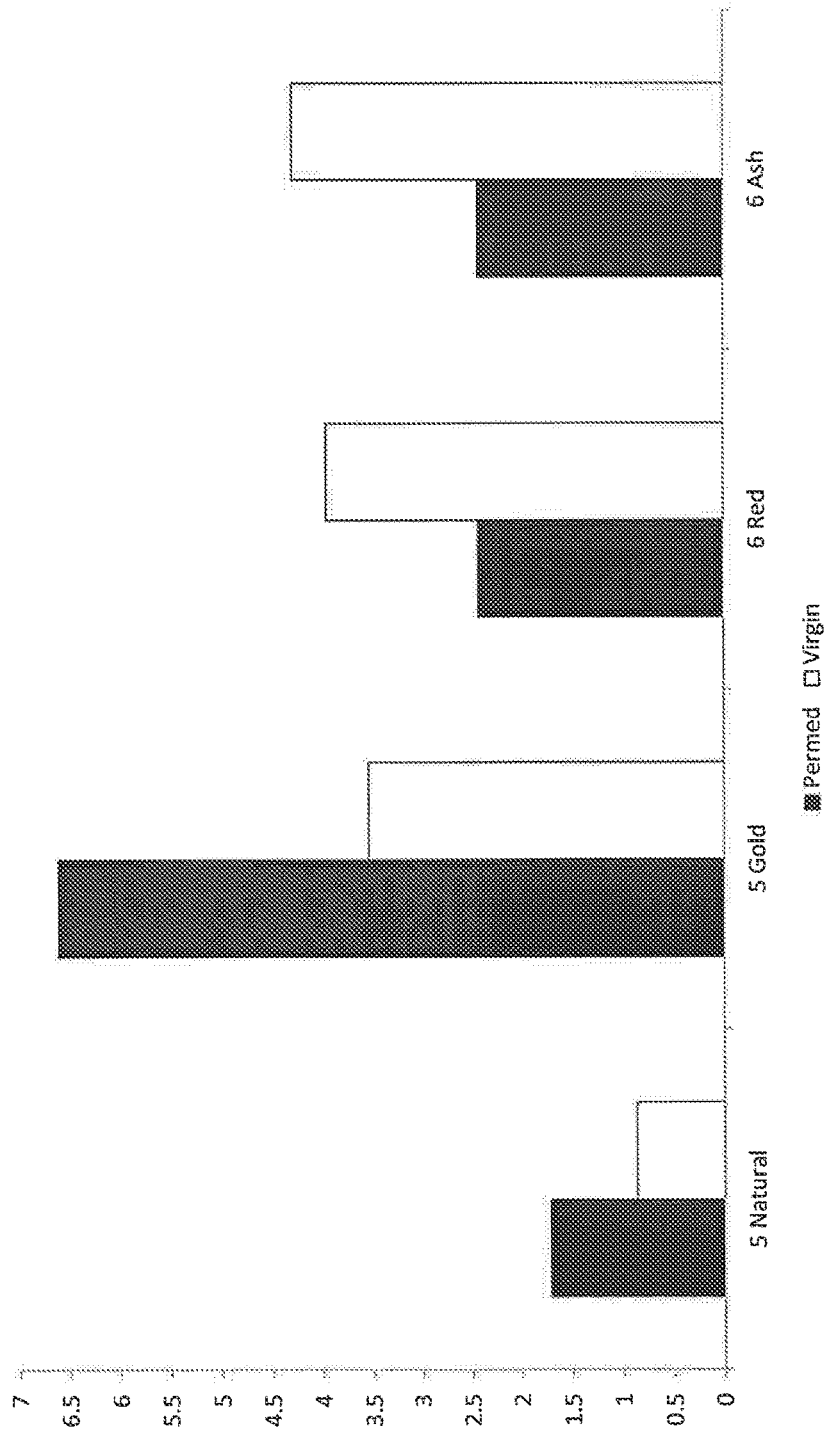
FIG. 3 shows ΔE measurements of water-in-oil emulsion compositions in accordance with one or more embodiments of the invention compared to commercial base compositions.
Figure 4:
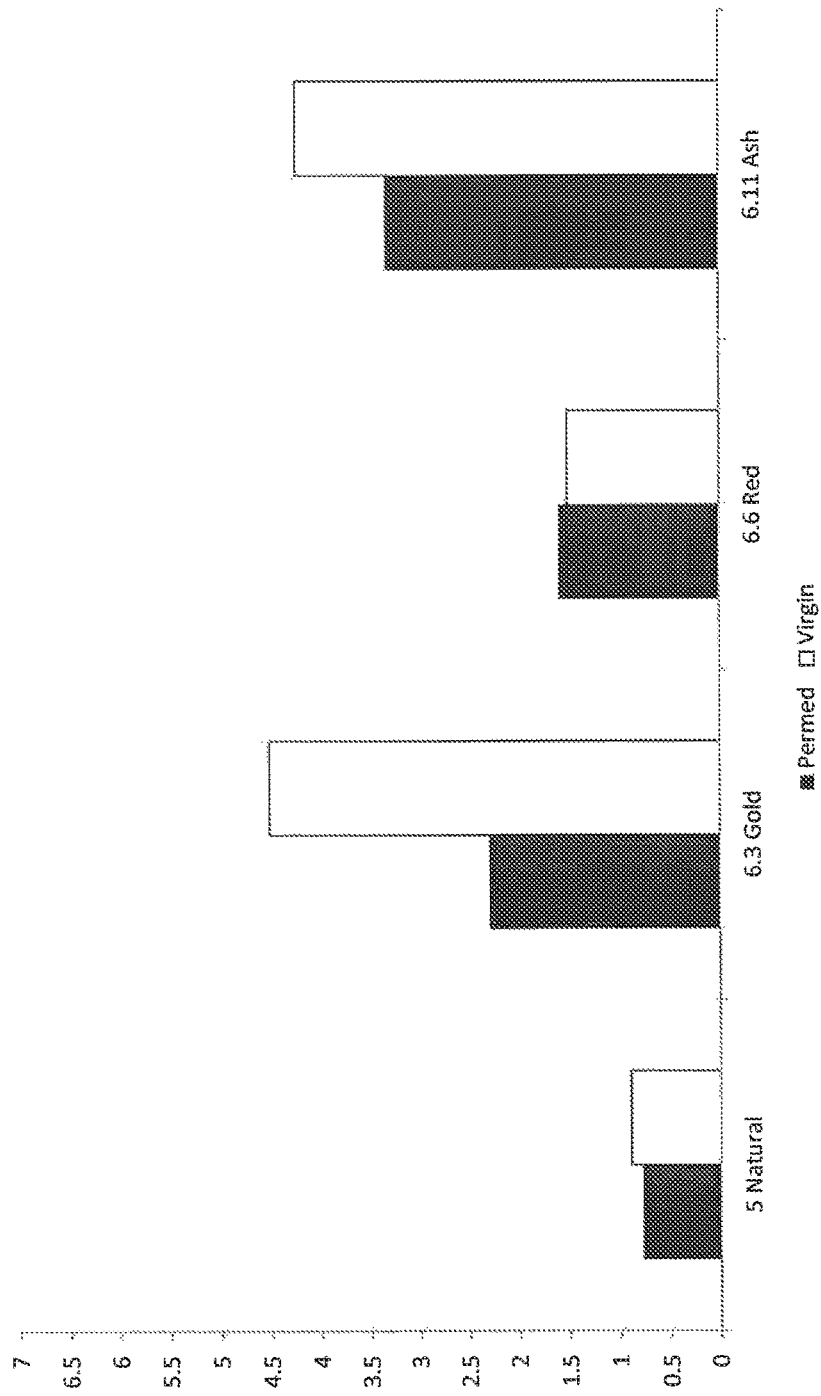
FIG. 4 shows ΔE measurements of water-in-oil emulsion compositions in accordance with one or more embodiments of the invention compared to commercial base compositions.

The above dye-containing formulations were mixed with developer (20 Vol.) applied to permed and virgin hair swatches and processed for 30 minutes. L*a*b values were then taken for the samples, and ΔE value calculated comparing the difference between the swatches dyed with the commercial bases versus the equivalent inventive water-in-oil inventive shade. The results are shown in FIGS. 3-4.

The shade results are interesting in that some reflects have very small ΔE values between the inventive formulae and benchmarks, but some reflects have larger ΔE values. The natural shades have small ΔE in comparison to both benchmarks. However, different reflects for each benchmark have large ΔE values. For the Commercial Line 1 shades, the ΔE is largest for the gold reflect.

The dyes for the gold reflect behaved differently in the W/O Cream base, resulting in a more mahogany reflect. For the Commercial Line 2 shades, the ΔE is largest for the ash reflect. The dyes for the ash reflect resulted in a grayer reflect for the W/O Cream rather than blue as in the Commercial Line 2 base.

These results are somewhat expected, as dyes are expected to behave differently in different bases. This is due to a variety of factors including the surfactant system, and the affinities and solubilities of each dye in the base. The rate of reaction is very important for achieving the desired reflects as reactions of primaries and couplers give specific reflects. Any change in the reaction speed due to interaction of the dyes with the base can cause a difference in reflect.

In conclusion, the inventive bases can hold heavy and complex dye loads, and has a viscosity suitable for bowl and brush during hair color application.

What is claimed is:

1. A hair color-altering composition comprising:
    a. an alkalizing agent;
    b. a dimethicone surfactant;
    c. a fatty alcohol having a $C_{16-36}$ alkyl group;
    d. an amphoteric surfactant;
    e. a waxy ether or a waxy ester; and
    f. a thickener,
wherein the composition is in the form of a water-in-oil emulsion.

2. The hair color-altering composition of claim 1, further comprising a hair colorant compound comprising an oxidation dye.

3. The hair color-altering composition of claim 1, wherein the composition has a pH of greater than about 7.

4. The hair color-altering composition of claim 1, wherein the alkalizing agent is selected from the group consisting of $NH_4OH$, monoethanolamine, and combinations thereof.

5. The hair color-altering composition of claim 1, wherein the composition comprises less than 20% by weight ammonia.

6. The hair color-altering composition of claim 2, wherein the oxidation dye is present in an amount of from about 0.05 to about 4% by weight.

7. The hair color-altering composition of claim 2, wherein the oxidation dye selected from the group consisting of para-phenylenediamines, bis(phenyl)alkylenediamines, para-aminophenols, ortho-aminophenols, heterocyclic bases, the addition salts thereof, and combinations thereof.

8. The hair color-altering composition of claim 1, wherein the dimethicone surfactant comprises an alkoxylated dimethicone.

9. The hair color-altering composition of claim 8, wherein the dimethicone surfactant comprises an alkoxylated dimethicone having ethoxy and/or propoxy groups.

10. The hair color-altering composition of claim 9, wherein the dimethicone surfactant has about 5-50 moles of ethoxy and/or propoxy groups.

11. The hair color-altering composition of claim 10, wherein the dimethicone surfactant has about 5-20 moles of ethoxy groups and 5-20 moles propoxy groups.

12. The hair color-altering composition of claim 1, wherein the fatty alcohol has an HLB value of less than 7.

13. The hair color-altering composition of claim 1, wherein the fatty alcohol has a $C_{18-26}$ alkyl group.

14. The hair color-altering composition of claim 1, wherein the amphoteric surfactant comprises an alkylamido alkylamine.

15. The hair color-altering composition of claim 14, wherein the alkylamido alkylamine comprises sodium cocoamphoacetate.

16. The hair color-altering composition of claim 1, wherein the waxy ether or waxy ester comprises PEG-30 dipolyhydroxystearate.

17. The hair color-altering composition of claim 1, wherein the thickener comprises hydrogenated vegetable oil, ozokerite, disteardimonium hectorite or combinations thereof.

18. The hair color-altering composition of claim 1, further comprising an inorganic salt.

19. The hair color-altering composition of claim 18, wherein the salt comprises calcium chloride, sodium chloride, magnesium sulfate, or combinations thereof.

20. The hair color-altering composition of claim 1, wherein the composition comprises:
    a. about 0.01 to 5% by weight of the hair colorant compound comprising an oxidation dye;
    b. about 0.01 to 15% by weight of the alkalizing agent;
    c. about 0.1 to 10% by weight of the dimethicone surfactant;
    d. about 0.1 to 10% by weight of the fatty alcohol having a $C_{16-36}$ alkyl group;
    e. about 0.1 to 10% by weight of the amphoteric surfactant;
    f. about 0.1 to 10% by weight of the waxy ether or waxy ester; and
    g. about 0.1 to 10% by weight of the thickener;
wherein the composition is a water-in-oil emulsion.

21. A hair color-altering composition comprising:
    a. about 0.05 to 5% by weight of an oxidation dye;
    b. about 0.01 to 15% by weight of an alkalizing agent;
    c. about 1 to 5% by weight of a dimethicone surfactant;
    d. about 1 to 5% by weight of behenyl alcohol;
    e. about 1 to 5% by weight of sodium cocoamphoacetate;
    f. about 1 to 5% by weight of a waxy ether or waxy ester; and
    g. about 1 to 5% by weight of disteardimonium hectorite,
    wherein the composition is a water-in-oil emulsion.

22. A kit comprising:
    a. a first container comprising the hair color-altering composition of claim 1; and
    b. a second container comprising a developer comprising hydrogen peroxide.

23. A method of altering the color of hair, the method comprising:
    a. applying the hair color-altering composition of claim 1 to hair.

24. A method of making a water-in-oil emulsion, the method comprising:
    a. preparing an oil phase by combining while heating:
        i. an oil base;
        ii. a dimethicone surfactant;
        iii. a fatty alcohol having a $C_{16-36}$ alkyl group;
        iv. a waxy ether or a waxy ester; and
        v. a thickener;
    b. preparing a water phase by combining while heating:
        i. water
        ii. an amphoteric surfactant
        iii. optionally, a salt
    c. adding the water phase into the oil phase and mixing the water phase and oil phase;
    d. optionally, adding additional thickener;

e. adding a hair colorant compound comprising an oxidation dye, wherein the composition is a water-in-oil emulsion.

25. The method of claim 24, further comprising adding a hair colorant compound comprising an oxidation dye after adding the water phase into the oil phase.

* * * * *